United States Patent [19]

Duinker

[11] 4,209,827
[45] Jun. 24, 1980

[54] APPARATUS FOR THE ELEMENT-WISE RECONSTRUCTION OF A TOMOGRAM OF A CROSS-SECTION OF AN OBJECT

[75] Inventor: Simon Duinker, Mollaan, Netherlands

[73] Assignee: N. V. Optische Industrie "De Oude Delft", Netherlands

[21] Appl. No.: 828,898

[22] Filed: Aug. 29, 1977

[30] Foreign Application Priority Data

Sep. 6, 1976 [NL] Netherlands .......................... 7609885

[51] Int. Cl.² ................................................. G01T 1/16
[52] U.S. Cl. .................................. 364/414; 250/445 T
[58] Field of Search .............................. 364/414, 415; 250/445 T, 363 S; 358/163, 166

[56] References Cited

U.S. PATENT DOCUMENTS

| | | | |
|---|---|---|---|
| 4,002,913 | 1/1977 | LeMay ............................ | 250/445 T |
| 4,044,240 | 8/1977 | Cox, Jr. et al. ................... | 250/445 T |
| 4,063,074 | 12/1977 | Wagner .............................. | 364/414 |
| 4,066,900 | 1/1978 | LeMay .............................. | 250/445T |

*Primary Examiner*—Errol A. Krass
*Attorney, Agent, or Firm*—O'Brien & Marks

[57] ABSTRACT

A system for reconstructing a tomogram or a portion thereof of a cross-section of an object. Modified signal profile data obtained by exposing the object to a substantially flat beam of penetrating radiation from different angles and by preprocessing the transmission radiation received at positions respectively corresponding to the different angles of incident radiation is stored in an analogue form into a collection of primary record paths, each of which is uniquely related to an associated angle of incident radiation; whereas such information elements stored in various of said primary record paths as are included in a secondary path that is uniquely defined by position coordinates determinative of the radiation absorption or density of a certain element of the object cross-section, are integrated.

13 Claims, 6 Drawing Figures

APPARATUS FOR THE ELEMENT-WISE RECONSTRUCTION OF A TOMOGRAM OF A CROSS-SECTION OF AN OBJECT

This invention relates to an apparatus for reconstructing a tomogram of a cross-section of an object irradiated with penetrating radiation, for example, X-rays, from a successive plurality of directions.

Our prior U.S. patent Application Ser. No. 795,238, filed May 9, 1977, now U.S. Pat. No. 4,164,657, gives proposals for the reconstruction of such a tomogram, starting from a collection of so-called signal profiles and using so-called back-projection.

If it is assumed that such an object cross-section is located in a plane superficies with the coordinates x and y, such a reconstructed radiation image can in principle be regarded as a distribution function f(x,y), which as a function of the position coordinates x and y represents, for example, the X-ray density of the object cross-sections to the radiation concerned or the distribution of radiation opacity. As primary data on the basis of which such a distribution function can ultimately be reconstructed is available, a collection of so-called signal profiles, which are each a measure for the variation in radiation absorption along the relevant object cross-section when the object is irradiated from a given direction in the x,y plane. These signal profiles are obtained as a result of relative rotary movement of, on the one hand, a combination comprising a source for producing an essentially flat beam of penetrating radiation and an opposed detector device, and an irradiated object carried between these, on the other. In this connection a signal profile is to be regarded as a series of absorption sum values produced when a flat, parallel beam of rays passes through the object from a given angle $\theta$ relative to the y axis. The absorption sum values along profile p for the beam direction $\theta$ vary from point to point according to a function of a variable u, or $p = p(u;\theta)$.

In this connection it is noted that in order to produce a tomogram of optimum resolution it is essential that the object is irradiated with a beam of parallel rays. As, for technical and economic reasons, it is always necessary to use a divergent beam, a certain auxiliary operation is required to achieve that the signal profiles p used as input data can be regarded as being generated by an imaginary beam of parallel rays. Such an auxiliary operation, so-called parallelization, and the means for performing such operations, form the subject matter of prior proposals as laid down in our U.S. Pat. application Ser. No. 814,989, filed July 12, 1977, now U.S. Pat. No. 4,168,435.

In order that, with the radiation used, the tomogram ultimately to be obtained may be a measure for the distribution of the density of the object in the cross-section under consideration, instead of being a measure for the absorption variation, the profiles relating to beams of parallel rays should subsequently be converted in known manner into so-called logarithmized parallel signal profiles, using a so-called logarithmic amplifier.

As indicated in our above prior Application Ser. No. 795,238, the back-projection and superimposition of such a collection of signal profiles result in a tomographic picture that is blurred as a result of inaccuracies of a point-spread function. For that reason, before being used for the contemplated reconstruction of the tomographic picture, these profiles must be pre-processed in a so-called pre-convolutor so that the resulting collection of new preconvoluted, logarithmized, parallel signal profiles $\bar{p} = \bar{p}(u,\theta)$, hereinafter briefly called modified signal profiles, after back-projection and superimposition provide the tomogram free from the point-spread function. Such an auxiliary operation, and the means for performing it, constitute the subject matter of prior proposals as described in our U.S. Pat. application Ser. No. 755,790, filed on Dec. 30, 1976 and now U.S. Pat. No. 4,097,898.

It is a general object of the present invention to provide alternative means, deviating from the proposals laid down in our Application Ser. No. 795,238, referred to above, for reconstructing a tomogram or tomogram portion corresponding to a pre-determined area of an object cross-section, starting from the modified signal profiles referred to above.

More in particular, it is an object of the present invention to provide means for reconstructing a tomogram or tomogram portion without back-projection as described in the above prior application Ser. No. 795,238, namely, by separately determining the elements thereof.

This possibility is of interest, for example, if it is desired to give a tomographic representation of pre-determined areas of one or more object cross-sections.

According to the invention, there is provided an apparatus for reconstructing a tomogram of a cross-section of an object irradiated with penetrating radiation, for example, X-rays, from a successive plurality of directions, which comprises means for providing signal profile data each representative of the variation in radiation absorption along the object cross-section from a given direction in the plane of said cross-section, and means for modifying such original signal profiles to produce a tomogram freed from a point-spread function, characterized by writing and addressing means for storing the offered modified signal profile data in a memory device, so that each modified signal profile is written into the memory device along a primary, continuously extending record path uniquely related to the direction of the original signal profile concerned; and integrating means coupled with said memory device and comprising pathway determining means, for producing a series of signal values each representative of the radiation absorption in, or the density of a given element of the object cross-section concerned, which integrating means is arranged to integrate the primary signal profile elements located along a secondary, continuously extending path, determined by said pathway determining means, and uniquely related to the position coordinates of the element concerned of the object cross-section.

An apparatus thus arranged in accordance with the present invention can be used with advantage, for example, when an analog tomographic representation is desired of an object cross-section or of a portion thereof that is considered of importance, as the density value given by the apparatus in analog format in accordance with the position coordinates of the elements of the object cross-section under consideration can be reproduced in analog format, such as, for example, displayed on the screen of a memory tube.

On the other hand an apparatus according to this invention offers the possibility of digitally processing the resulting elementary density values, so that, for example, if desired by means of a computer with an associated memory in which these density values with their associated coordinates are stored, certain parts of the tomogram can be examined in detail using known per se programs. In this connection we contemplate, for example, an image of lines of equal density, contrast analysis, and the like. In connection with such purposes, it is a further feature of the apparatus according to this invention that the output of said integrating means is connected to an analog-to-digital converter for converting each of the signal values supplied in analog format to a corresponding digital format, and said pathway determining means are coupled with a second analog-to-digital converter for converting the pathway information available in analog format into a corresponding digital format.

With such an organization it is accordingly possible, notwithstanding the fact that the signal values representative of density values and the profiles have been obtained by analog means, to realize the image reconstruction of the ultimate, optionally complete or partial tomogram element by element in a manner conventional in CAT (computer aid tomography) systems, naturally with all the possibilities of using the software developed and available therefor.

A preferred embodiment of the present invention is characterized in that the addressing and writing means coupled with said memory device are so arranged that said primary paths are successively written in, in a radial sense, from a memory address selected as the origin of a system of coordinates and corresponding to the axis of relative rotation of the object, as straight paths transverse to the direction of the parallel radiation; and said integrating means are arranged to serially integrate elements of the signal profiles thus read-in along a circular path extending through said memory address, the diameter and angular position of which circle is determined by the position coordinates of the image element corresponding to the location of a relevant object cross-section element.

Further objects and features of the invention will become apparent as the description proceeds with reference to the accompanying drawings.

In said drawings.

Figure 1:
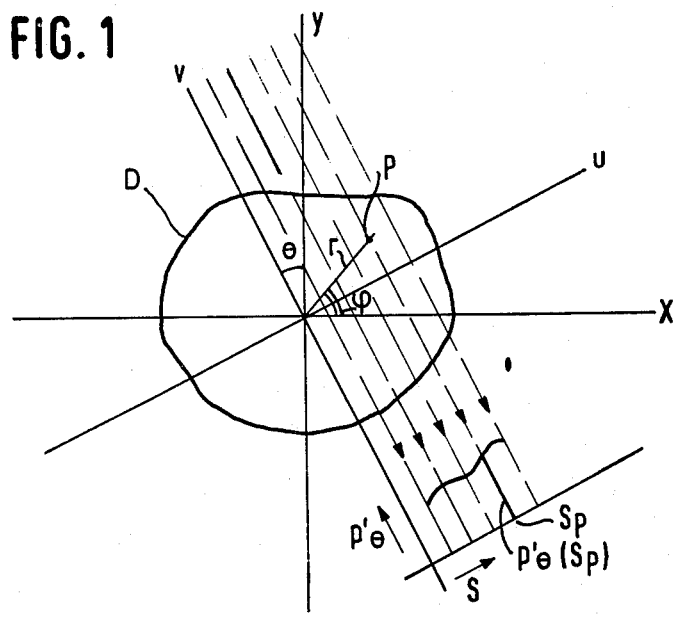
FIG. 1 is a diagrammatic representation of an object cross-section D in an x,y plane.

Referring now to FIG. 1, there is shown an object cross-section D in an x,y plane. This object cross-section is irradiated with a penetrating beam of parallel rays s impinging at an angle $\theta$ to the y axis. A tomogram or a two-dimensional image of such an object cross-section, can in principle be described by a distribution function f(x,y), in which x and y are the coordinates in a rectangular system of coordinates in the x,y plane concerned. This distribution function is representative of the variation in density to the radiation used across the cross-section of the object. A flat beam of parallel rays irradiating the object provides, in a detector device positioned perpendicular to the direction of the rays, a profile signal $p'_\theta$. In it, a profile element $p'_\theta(s_P)$ is the total absorption by the object of the ray $s_P$ passing through point P. Logarithmization of the signal causes the value $p'_\theta(s_P)$ to be converted into $P''_\theta(s_P) = \ln p'_\theta(s_P)$, being the sum of the densities of all elements of the object along this ray $s_P$. In order to learn the density to the radiation in a given point P on ray $s_P$, we should regard from the collection of profiles produced by varying the angle of incidence $\theta$ through a range of from 0 to $2\pi$, the sub-collection relating to all rays s passing through point P, i.e., the sub-collection $p''_\theta(s_P)$ in which $\theta = 0 \to 2\pi$. If, in accordance with the proposals laid down in the afore-mentioned U.S. Patent Application Ser. No. 795,238, such a sub-collection is projected back into the memory device, taking into account the angle of incidence $\theta$, this results in a total signal in a point corresponding with point P. This total signal, although being representative of the density of the object in P, comprises additionally contributions from the density of all other points of the object. In other words, the density value in P is blurred by the point-spread function. In order to meet this disadvantage it is proposed in said prior application to start from pre-processed profiles $p_\theta$, obtained by convoluting each element one by one with a suitable function, the arrangement being such that back-projection of the pre-processed profiles $p_\theta$ results in a tomogram freed of the inaccuracies of a point-spread function.

Now, the present invention offers the possibility of reconstructing a tomogram or tomogram portion, starting from such pre-processed profiles, without such a back-projection. In other words, the present invention starts with modified signal profiles, i.e. logarithmized, parallelized, and pre-convoluted signal profiles, the signal profiles so modified being designated by $\bar{p}(\theta)$.

Figure 2:
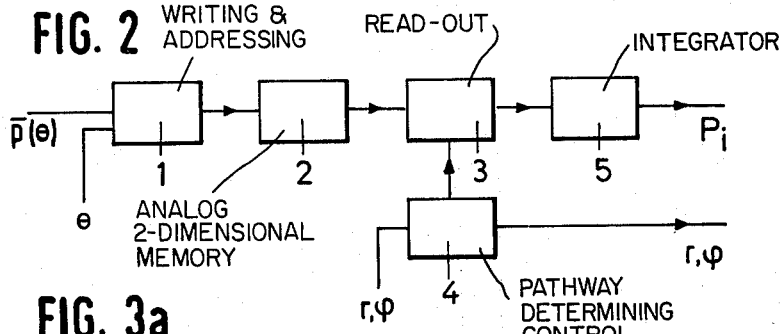
FIG. 2 is a block diagram of a basic embodiment of an apparatus according to this invention.

FIG. 2 illustrates, in the form of a block diagram, a basic embodiment of an apparatus according to the present invention. As stated before, the apparatus starts with logarithmized, parallelized and pre-convoluted signal profiles $\bar{p}(\theta)$, and also with the angle data $\theta$, i.e., the angle at which each beam of parallel rays passes through the object relative to a reference axis. The modified signal profile data $\bar{p}(\theta)$ and the associated angle data $\theta$ are supplied to writing and addressing means 1 serving to write the modified signal profile data into a memory device 2. The addressing means are arranged so that, in response to the supplied angle data $\theta$, the data corresponding to a modified signal profile is entered into the memory device along primary, continuously extending records paths, each such path being uniquely related to the direction of the signal profile concerned. On the other hand the memory device 2 is coupled to a read-out device 3 under the control of a pathway determining device 4. Thus it is possible for the data written into the memory device to be read out along a path determined by control device 4, and the data available at the output of read-out device can then be integrated by an integrator 5. The path or paths along which the stored data are read out is or are determined by position data supplied to pathway determining device 4. These position data define the relevant elements of a cross-sectional area to be examined. For example, these position coordinates may be given as polar coordinates r,$\phi$ determinative of a cross-sectional element, for example, P (FIG. 1). Each such a cross-sectional element r,$\phi$ determines a read-out path along which read-out device 3 reads memory device 2 under the control of device 4 to provide a signal value $P_i$, produced by integrator 5, which is determinative of the radiation absorption in the cross-sectional element r,φ concerned. Thus a tomogram for a desired series of cross-sectional elements r,φ can be reconstructed element by element.

In this arrangement, integrator 5 gives the relevant signal value determinative of the radiation absorption in a given element of the object cross-section in analog format, which is also the case for the position data that can be derived from the pathway determining device 4.

The density data $P_i$ and position data r,φ can be processed further either by analog processing or digital processing.

Figure 3A:
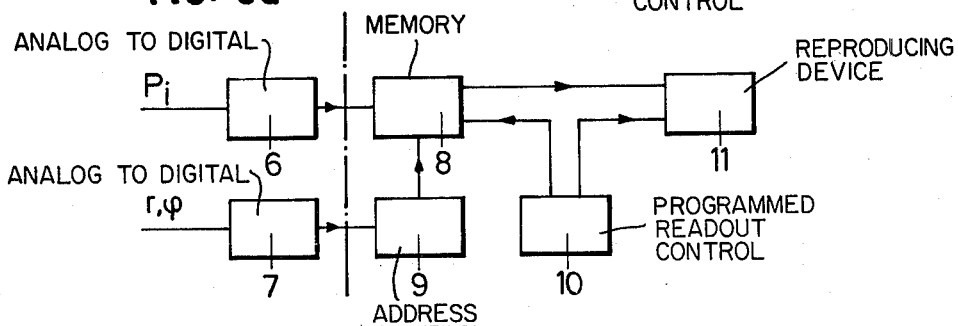
FIG. 3a is a block diagram for an embodiment for digital processing.
Figure 3B:
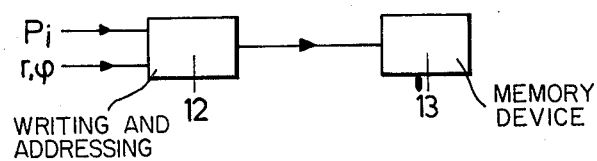
FIG. 3b is a block diagram for an embodiment for analog processing.

FIG. 3a gives a block diagram for an embodiment for digital processing, and FIG. 3b gives a block diagram for an embodiment for analog processing.

In the embodiment illustrated in FIG. 3a, the output of integrator 5 is coupled to a first analog-to-digital converter 6, the position data derived from pathway determining device 4 being fed to a second analog-to-digital converter 7. The density data brought into digital format by converter 6 is then written into a digital memory device 8, and this under the control of an addressing device 9 connected thereto, which performs the writing control action in response to the position data r,φ brought into digital format. By means of a programmed control 10, the digital data written into memory device 8 can then be read out in the desired manner and be reproduced in digital format by a reproducing device 11. Thus it is possible, using known per se and available software, to make a desired detailed examination of parts of a tomogram.

It is of advantage to combine the first and second converter 6 and 7 with an arrangement having the configuration shown in FIG. 2 to form a unit, as such a unit makes possible simple adaptation, in a technically and economically attractive manner, to existing digital processing systems used for tomographic purposes.

In the embodiment of FIG. 3b, the density data $P_i$ available in analog format and the position data r,φ are supplied direct to a writing and addressing device 12, which can write the density values P into an analog memory device 13 at the addresses indicated by device 12. In this way an analog tomogram can be reconstructed element by element from the selected cross-sectional elements r,φ in a simple manner.

In the embodiment of FIG. 3a, the memory device 8 may, for example, take the form of a core memory, while in the embodiment of FIG. 3b, memory device 13 may be formed as a memory tube. Thus in a suitable embodiment the memory device comprises a memory tube, the viewing screen of which has a persistence adapted to the total integration time required; and said integrating means comprises a photo-electric element for receiving a light image as formed by an optical reading device mounted in opposition to said viewing screen and arranged to form a light image of the viewing screen surface corresponding with a secondary path.

Memory device 2 may take several forms. In one embodiment, memory device 2 comprises an image conversion tube, on the target plate of which the signal profiles offered are written according to the primary record paths using an electron beam and under the control of deflection electrodes. The data thus written on the target plate can be read non-destructively using the same electron beam or a different electron beam, depending on the kind of image conversion tube used, the pathway determining device being formed by the control for the electron beam deflection of the image conversion tube.

In a different embodiment, memory device 2 comprises a memory tube, into which the signal profiles offered may be written in a conventional manner. The data thus written-in can be read by opto-electrical means using an opto-electrical detector disposed behind a mask forming part of the pathway determining device. A desired read-path configuration can then be realized using the movement and shape of aperture of this mask in combination with an optical system. For instance, use can be made of an optical reading device which includes a mask having an annular optical transmissive window having a fixed diameter; an optical system with a continuously variable magnification, mounted in the optical path of said window; and control means for adjusting the magnification of said optical system in accordance with the position coordinates of the object cross-section element concerned.

When memory device 2 comprises such a memory tube, the data written into it may also be read by means of a known per se image recording tube, such as a vidicon or an isocon. A pathway determining device is then formed by the electron beam deflection control of the recording tube itself, by means of which control the desired read-out path configuration can be obtained.

Figures 4, 5:
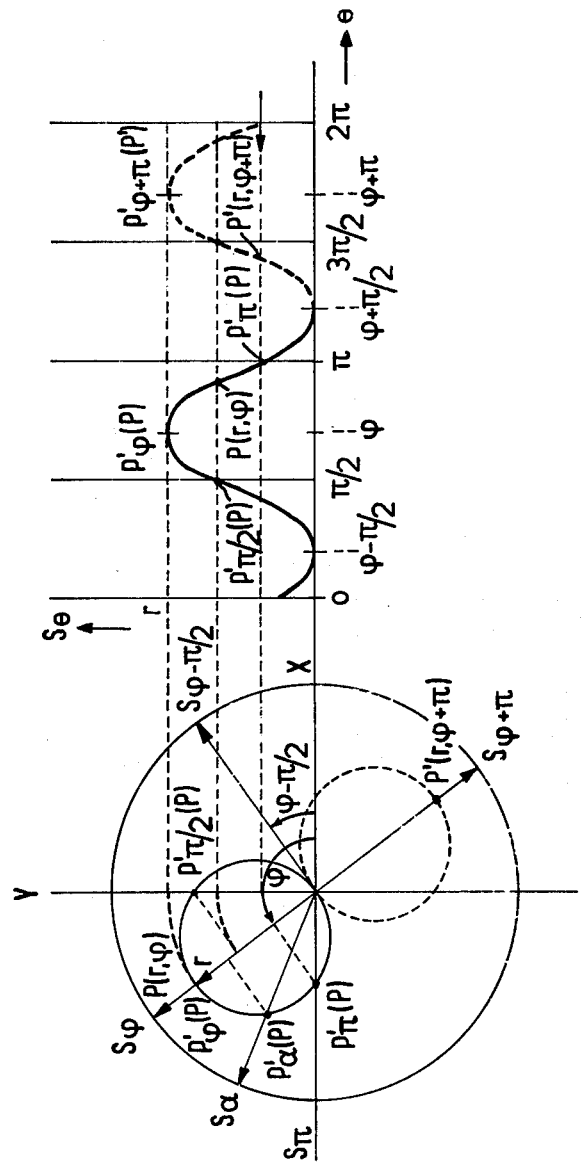
FIGS. 4 and 5 are diagrams of writing and reading paths illustrating the signal processing in preferred embodiments of the invention wherein the density values for two diametrically opposed elemental areas of a cross-sectional object slice under consideration can be produced simultaneously.

In a simple embodiment of the present invention, the writing and addressing device 1 is so arranged that the primary record paths are successively written in, in a radial sense, from a memory address selected as the origin of a system of coordinates and corresponding to the axis of relative rotation of the object, as straight paths transverse to the direction of the parallel radiation. When the signal profiles offered are thus written, the radiation absorption for a given element of the object cross-section can be obtained by integrating along a circular path passing through said origin, the diameter and angular position of said path being determined by the pole coordinates defining the relevant element of the object cross-section. In order to increase the rate of processing, integration may be effected simultaneously along two externally touching circles, whereby the density values for two diametrically opposed elements of the object cross-section are produced simultaneously. In FIG. 4, this arrangement is illustrated for two diametrically opposed elements $P(r,\phi)$ and $P'(r,\phi+\pi)$. The circular paths along which the stored signal profiles are read are respectively indicated by a fully drawn line and a dash-line; these paths are traversed either simultaneously or one immediately after the other.

It will be clear that when the signal profiles offered have been written along straight lines extending through the origin, as described hereinbefore, elements of a cross-section being examined that are located along the same line are to be integrated according to circular paths touching each other in a same point and having a diameter corresponding to the radius-coordinate of the element concerned of the cross-section. Such a path configuration may also be realized by optical means, for example, using a mask with an annular aperture that can be projected on to a photo-sensitive detector by means of an optical system with variable magnification. The magnification of the optical system is then set to match the radius-coordinate of the element concerned of the object cross-section.

The data required for the writing and addressing device 1 to write the primary rectilinear paths in a radial sense and in accordance with the direction of the relevant original signal profile can be derived from an electro-mechanical converter capable of converting data concerning the angular position of the combination of the radiation source and the detector relative to the object to be examined into corresponding electrical signals.

Naturally the invention is not limited to the writing and integration along the primary and secondary paths described hereinbefore. It is also possible to have the primary paths extend along straight parallel lines spaced proportionally to the position angle of the radiation source, the secondary paths being sinusoidal with the phase and amplitude corresponding to the position coordinates of the element concerned of the cross-section. This arrangement is illustrated in FIG. 5, which is to be considered in conjunction with FIG. 4. In both cases the value of the modified signal profile $p'_\theta(S)$ is plotted along $S_\theta$. In the vertical position thereof, they are in fact three-dimensional representations in the $\theta, S, p$ space. As the secondary paths are sinusoidal, the deflection may have a fly-back, as indicated by the arrow pointing to the left in FIG. 5, each time becoming operative with the suitable phase. Just as in the arrangement of FIG. 4, sinusoidal secondary paths allow of producing the opacity values for two diametrically opposed elements, such as P and P' either simultaneously or one immediately after the other, and this by reading for P during one half-cycle of the sine and for P' during another half-cycle. This is indicated by fully drawn lines and dashed lines, respectively. By keeping the amplitude constant and letting $\phi$ increase, the opacities of elements $P(r, \phi \pm \Delta\phi)$ and $P'(r, \phi + \pi \pm \Delta\phi)$ are found, which are located on a circle having radius r and 0 being the centre. By letting the amplitude increase and keeping $\phi$ constant, the opacities of elements $P(r \pm \Delta r, \phi)$ and $P'(r \pm \Delta r, \phi + \pi)$ are found, respectively located on the radius vector of P and P'. For a point located within the plane of the cross-section and outside the object, the value $\pi\phi(P) = 0$. If the pre-convolution is exact, the circular integral should also be $\equiv 0$, although there may be positive an negative contributions in a particular pathway.

I claim:

1. An apparatus for use in reconstructing a tomogram of a cross-sectional planar slice of an object from logarithmized, parallelized and pre-convoluted analog signal profiles, each profile including a plurality of data points corresponding to absorption of object points along parallel radiation lines forming a flat beam of penetrating radiation in the plane of the slice at a respective exposure angle of rotation about an axis perpendicular to the plane of the slice, the apparatus comprising a memory device suitable for receiving and storing analog data in a two-dimensional arrangement, writing and addressing means for storing the logarithmized, parallelized and pre-convoluted analog signal profiles in the memory device along respective primary continuously extending paths uniquely related to the respective exposure angles, readout means associated with said memory device, readout pathway determining means for controlling said readout means to readout respective series of signal values in the memory device along respective secondary continuously extending paths crossing the primary paths and uniquely related to the respective object points, and integrating means for integrating the respective series of signal values corresponding to the respective object points to produce object signals.

2. An apparatus according to claim 1 including a first anolog-to-digital converter connected to the output of said integrating means for converting each of the object signals into corresponding digital signals; and a second analog-to-digital converter coupled to the readout pathway determining means for converting pathway data offered in analog format into a corresponding digital format.

3. An apparatus according to claim 1 wherein said addressing and writing means is arranged so that said primary path are successively written in paths extending radially from a memory address location selected as the origin of a system of coordinates and corresponding to the axis of relative rotation of the object, said primary paths being straight paths; and said readout pathway determining means is arranged to cause said secondary paths to be circular paths, the diameters and angular positions of which circular paths are determined by the position coordinates of respective image elements corresponding to the location of respective object points.

4. Apparatus according to claim 3, wherein said readout pathway determining means is arranged so as to read the stored signal profiles along two circular paths extending through said memory address location, said circular paths having aligned diameters extending through said memory address location; and said integrating means is arranged to generate two separate output signals.

5. Apparatus according to claim 4 wherein said readout pathway determining means is arranged to read the stored signals along the two circular paths simultaneously.

6. Apparatus according to claim 4 wherein said readout pathway determining means is arranged to read the stored signal profiles along the two circular paths one immediately after the other.

7. Apparatus according to claim 1 wherein said writing and addressing means is arranged so that said primary paths are straight, parallel primary paths spaced a distance proportional to the angle from which the object cross-section is irradiated; and said pathway determining means is arranged so that said secondary paths are sinusoidal paths intersecting said parallel paths, the phase and amplitude of said sinusoidal paths being determined by polar coordinates of image elements corresponding to the location of the respective object points.

8. Apparatus according to claim 7 wherein said readout pathway determining means is arranged to read the stored signal profiles along two contiguous halves of a sinusoidal path; and said integrating means is arranged to issue two separate output signals.

9. Apparatus according to claim 8 wherein said readout pathway determining means is arranged to read the stored signal profiles along the two contiguous halves of the sinusoidal path simultaneously.

10. Apparatus according to claim 8 wherein said readout pathway determining means is arranged to read the stored signal profiles along the two contiguous halves of the sinusoidal path one immediately after the other.

11. Apparatus according to claim 1 wherein said memory device includes a memory tube, the viewing screen of which has a persistence adapted to the total integration time required.

12. Apparatus according to claim 1 wherein said memory device includes a memory tube, the viewing screen of which has a persistence adapted to the total integration time required; and said readout means includes an image recording tube, such as vidicon, disposed in opposition to said viewing screen the scanning ray controlling means of said image recording tube being arranged to read the photocathode thereof according to a secondary path as defined hereinbefore.

13. Apparatus according to claim 1 wherein said memory device includes an electronic image conversion tube having a target plate on which said signal profiles are to be written, and said pathway determining means are operable to read said target plate according to the secondary path as defined hereinbefore.

* * * * *

UNITED STATES PATENT OFFICE
CERTIFICATE OF CORRECTION

Patent No. 4,209,827　　　　　Dated　June 24, 1980

Inventor(s)　Simon Duinker

It is certified that error appears in the above-identified patent and that said Letters Patent are hereby corrected as shown below:

On the cover page, the inventor's address should be -- Bloemendaal, Netherlands --.

Signed and Sealed this

Fourth Day of November 1980

[SEAL]

Attest:

SIDNEY A. DIAMOND

Attesting Officer　　Commissioner of Patents and Trademarks